United States Patent [19]

Bagshawe et al.

[11] E Re. 30,627

[45] Reissued May 26, 1981

[54] APPARATUS FOR PERFORMING CHEMICAL AND BIOLOGICAL ANALYSIS

[75] Inventors: Kenneth D. Bagshawe, London; James E. Kemble, Burgess Hill, both of England

[73] Assignee: Picker Corporation, Cleveland, Ohio

[21] Appl. No.: 784,648

[22] Filed: Apr. 4, 1977

Related U.S. Patent Documents

Reissue of:

[64] Patent No.: 3,923,463
Issued: Dec. 2, 1975
Appl. No.: 404,720
Filed: Oct. 9, 1973

[30] Foreign Application Priority Data

Oct. 9, 1972 [GB] United Kingdom ..... 46521/72

[51] Int. Cl.[3] ..... G01N 31/00; G01N 33/56

[52] U.S. Cl. ..... 23/230 R; 23/230 B; 23/230.3; 23/920; 422/63; 422/66; 422/71; 422/101; 210/387

[58] Field of Search ..... 23/253 R, 259, 230 R, 23/253 TP, 230 B, 230.3, 920; 250/328; 210/238, 344, 346, 486, 387; 422/63, 65, 66, 69, 71, 81, 101

[56] References Cited

U.S. PATENT DOCUMENTS

| | | | |
|---|---|---|---|
| 3,138,015 | 6/1964 | Avery | 210/387 X |
| 3,193,358 | 7/1965 | Baruch | 23/253 R |
| 3,193,359 | 7/1965 | Baruch et al. | 23/253 R X |
| 3,487,862 | 1/1970 | Soderblom | 23/259 X |
| 3,525,591 | 8/1970 | Jungner et al. | 23/253 R |
| 3,526,480 | 9/1970 | Findl et al. | 422/66 |
| 3,544,272 | 12/1970 | Vaills | 23/259 X |
| 3,607,090 | 9/1971 | Maxon | 23/259 X |
| 3,615,257 | 10/1971 | Frost et al. | 210/447 X |
| 3,620,678 | 11/1971 | Gulgan | 23/259 X |
| 3,663,374 | 5/1972 | Moyer et al. | 23/253 TP UX |
| 3,749,916 | 7/1973 | Thomas et al. | 250/328 X |
| 3,784,826 | 1/1974 | Bagshawe et al. | 250/328 |
| 3,825,410 | 7/1974 | Bagshawe | 422/101 X |
| 3,888,770 | 6/1975 | Avital et al. | 210/238 |

FOREIGN PATENT DOCUMENTS

| | | | |
|---|---|---|---|
| 929079 | 6/1963 | United Kingdom | 210/387 |

*Primary Examiner*—Arnold Turk
*Attorney, Agent, or Firm*—Scrivener, Clarke, Scrivener and Johnson

[57] ABSTRACT

A system for the automated analysis of large numbers of liquid samples, in which a multiplicity of sample tubes are loaded in racks into a cassette and the loaded cassette is transferred from station to station, with operations of sample insertion, dilution, reagent addition and withdrawal for filtering being performed at successive stations. At each station there is a separate processing module adapted to receive the cassette, each module including the apparatus necessary for performing one of the abovementioned operations on each individual sample tube when it is located at a particular operational location in the cassette. Each module also has members for shifting the racks in the cassette in such manner that all tubes pass through the operational location in turn while strictly maintaining the same order of sequence throughout the operations.

54 Claims, 4 Drawing Figures

APPARATUS FOR PERFORMING CHEMICAL AND BIOLOGICAL ANALYSIS

Matter enclosed in heavy brackets [ ] appears in the original patent but forms no part of this reissue specification; matter printed in italics indicates the additions made by reissue.

This invention relates to a system of analysis and automated apparatus for the techniques of competitive protein binding including radioimmuno assay and radiometric assay. These techniques are widely used to measure the concentration in liquids of substances hereinafter described as "the ligand" which bind to specific antibodies or other macromolecules hereinafter described as "specific antibody".

Ligand of the species to be measured, labelled with a radioisotope, is added to a reaction tube containing a quantity of the unknown sample liquid, before or after the addition of specific antibody. The labelled ligand and the ligand in the unknown sample compete for binding to the specific antibody. In similar tubes, in each assay, known concentrations of unlabelled ligand are included to provide reference standards. The amount of ligand is determined by separating [antibody bound] *antibody-bound* ligand from free ligand by centrifugation or filtration and by counting the amount of labelled ligand in the precipitate or liquid phase.

To perform such reactions accurately, it is necessary to dispense the sample and reagents accurately, to ensure complete mixing of reagents and diluents, to incubate all samples and reference standards for the same time at the same temperature and to separate [antibody bound] *antibody-bound* ligand from free ligand efficiently. It is necessary to present reaction tubes in orderly sequence at one or more locations for these operations, to carry these tubes from one location to another, to maintain their initial sequence and to occlude the open end of the tubes to prevent spillage and evaporation. Competitive protein binding assays have been described for several hundred substances and a laboratory may need to use many different assay protocols and to assay batches of very variable size.

Existing apparatus provides arrangements for dispensing samples and reagents into tubes located in carrier racks. Such racks readily get out of sequence and sample identification by manual methods is tedious and inconvenient. Means for diluting samples by constant ratios also exist but existing automatic devices do not allow for variation of ratio from sample to sample, nor do they readily perform serial dilutions as required for reference standards. The rate limiting stage in competitive protein binding assays is generally that of isotope counting which is performed conventionally by nucleonic counters with automatic sample changers. The use of computers has hitherto been limited to performing calculations on data output by nucleonic counters and this entails feeding in sample identification data in addition to the preparation of the initial work sheet.

A hitherto known system provides the means for individually adjusted dilution ratios and for serial dilutions in dilution containers and analysis performed in conveyor belts of incubation pots. This system, however, is an integrated operation which allows no interruption between sample input and data output so that variation of assay protocol, incubation time and counting time is severely restricted and this limits the rate of throughput of samples and applicability of the system.

According to the present invention, there is provided apparatus for analysing a plurality of liquid samples, each sample being in a container or tube, such that a linear series of such tubes forms a rigid or semi-rigid rack, and comprising a cassette within the shell of which a plurality of such racks are to be contained said cassette having apertures in its walls, through which means, operated by apparatus external to the cassette, actuate and advance the racks and tubes sequentially and stepwise past a fixed point and such that a cassette be freely removable from the operating apparatus without disturbing or removing the contained racks and tubes so as to be transportable to other locations, the initial sequence of tubes and racks being maintained throughout.

The present invention facilitates the analysis of samples in small or large batches, permits wide choice of volume and dilution ratio for each sample, choice of volume and sequence of addition of reagents and choice of assay protocol. Further, it minimises the time required for documentation and provides a high rate of sample throughput.

The equipment may include two teleprinters and six modules, five of which are, for convenience, arranged together to form the sample processing unit whilst the sixth module is described as the control unit.

As already specified, multiple tubes are located in a multiplicity of racks which in turn are located within a cassette. The cassettes can be transferred manually between different modules. These features permit all the tubes for one assay to be kept together, the initial sequence of tubes to be rigidly maintained and the simultaneous processing of different assays employing wide variation in analytical protocol.

Another novel feature in the preferred embodiment of the invention is the control unit which is programmed to control the operations of the modules. This unit also counts simultaneously the radioactivity from a multiplicity of reactions and is programmed to compute the results of assays from these counts and to present the data in any desired form at the appropriate terminal. This feature greatly increases the throughput of the assay system whilst reducing the number of controls on the processing units. It further avoids the use of a plurality of nucleonic radioactivity counters such as ratemeters or scalers, reduces the opportunity for human error and minimises documentation.

An apparatus and system according to the invention will now be described in some detail by way of example and with reference to the accompanying drawings, in which.

Figure 1:
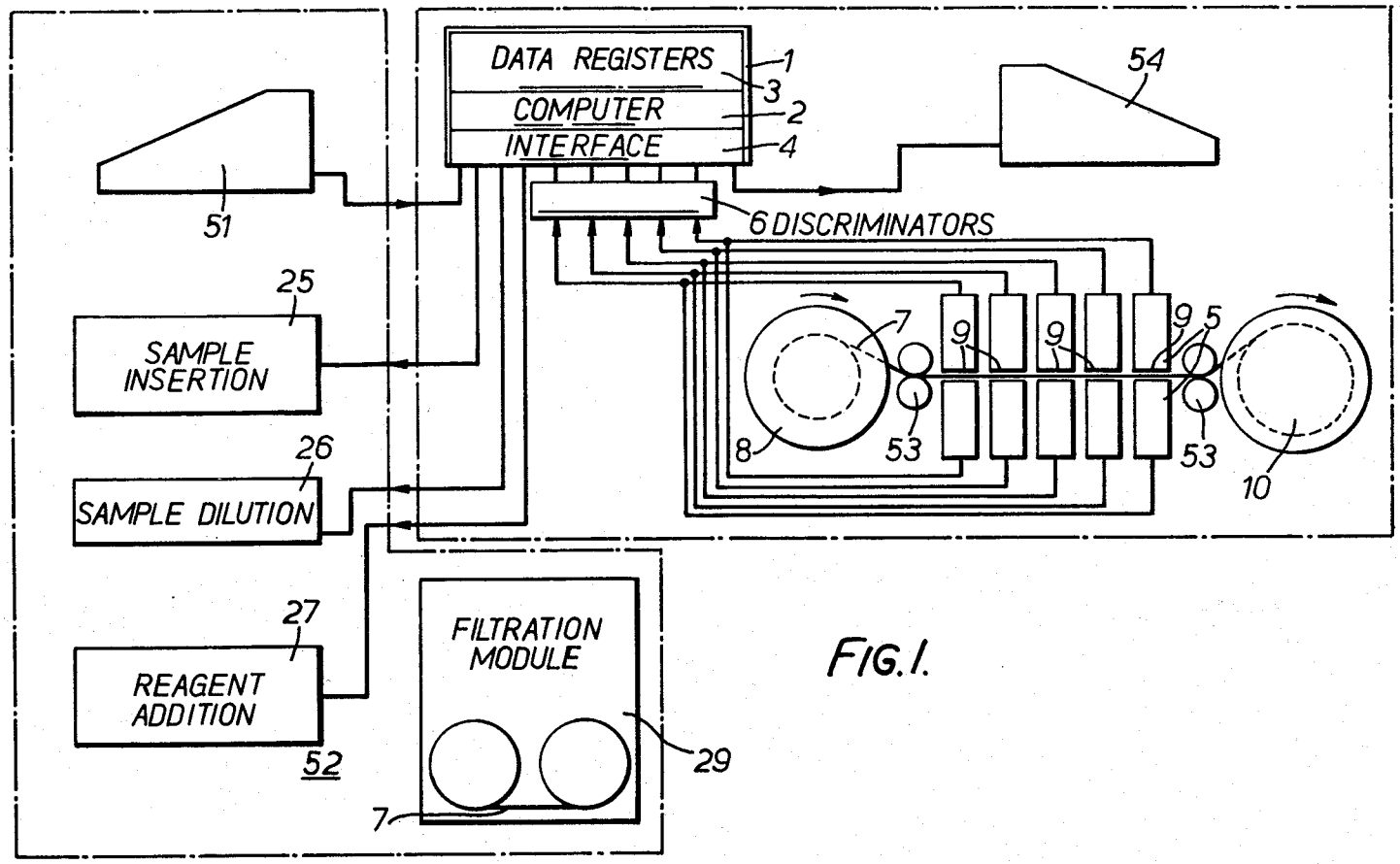
FIG. 1 is a block diagram of the overall system.

Referring firstly to FIG. 1, the control unit 1 incorporates a small on-line computer 2 with electronic data registers 3 and interface unit 4, radioactivity counting locations 9 defined between two rows of photomultiplier units 5 arranged in pairs and connected to corresponding discriminator units 6 that feed signals to the interface, and means for advancing tape 7 bearing radioactive locations from a supply spool 8 to the counting locations 9 and thence to a take up spool 10.

The control unit is programmed by three classes of data. Class I data pertain to the instruction and operational language of the computer unit and identification of storage locations in its data register and these are normally stored permanently within the data register. Class II data pertain to the analytical procedure and protocol for a specific assay and are normally input at the beginning of any assay operation. Class III data pertain to individual samples within an assay and are input by the operator during the first stage of each assay.

Data are input via any suitable terminal but a teleprinter 51 with paper tape punch and reader is the preferred form. Data are stored in two ways. Data controlling functions, such as dispensing, transferring and dilution by the sample processing unit 52, are retained in the electronic data register 3 of the control unit 1. These data, together with all other data relating to an assay, are stored as a punched tape which is prepared during the course of the sample input. The paper tape is retained for use at a later stage in the analysis. In addition, all Class II and III data are typed out by the input teleprinter 51 using a simple conversational language to provide the work record. No further records or data input are required of the operator. The remaining functions of the control unit will be described after the cassette and sample processing modules.

Figures 2, 3:
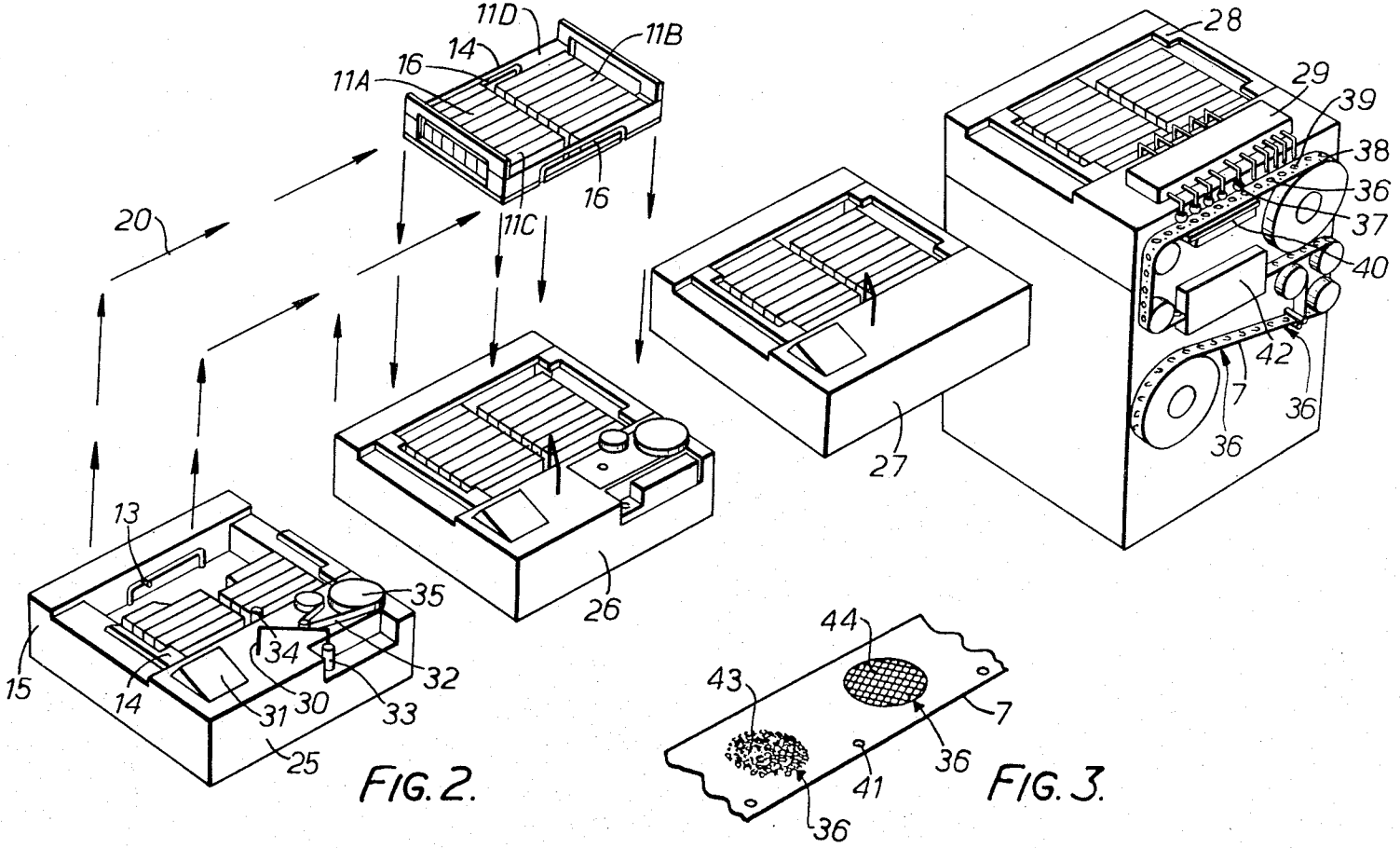
FIG. 2 is a pictorial diagram showing detail of a sample processing unit of the system of FIG. 1.
FIG. 3 is a detail of filter tape employed in the system.
Figure 4:
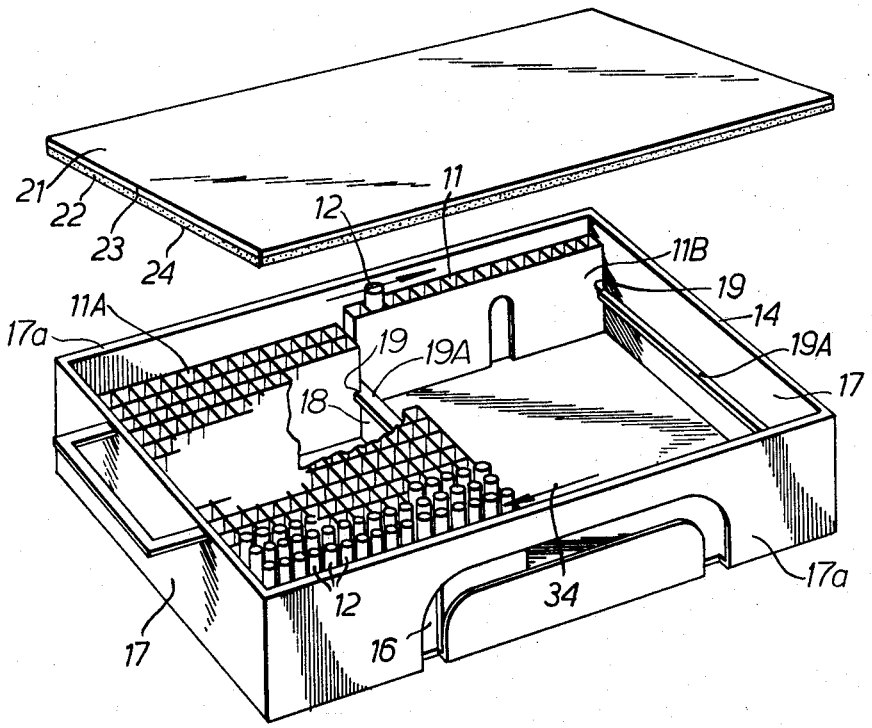
FIG. 4 is a diagrammatic pictorial view of a cassette holding reaction tubes.

Referring now to [FIG.] *FIGS. 3 and* 4, showing a cassette 14 containing reaction tubes for samples to be processed, part of the technique to be described is based on a principle of moving *linear arrays of sample containers comprising* racks 11, holding tubes 12 at uniform pitch, stepwise past a fixed operation point 34. The racks are of uniform length and are arrayed within the shell or cassette 14 in two [bands] *banks* 11A, 11B. Each bank consists of a plurality of racks 11 placed side by side along their long sides. The racks in the two banks are more or less end to end but are so staggered that the front rack of one bank and the rear rack of the other bank are free to move endwise *into spaces 11C and 11D at the opposite ends of the respective banks 11A and 11B (FIG. 2)* and thus be moved from one bank to the other. Such a movement is carried out stepwise by levers and pushrods *13* in [the] *a cassette support means at a first station comprising* base module 15 (FIG. 2) which *removably* receives the cassette 14 and these *levers and pushrods 13*, operating through apertures 16 in the walls of the cassette, move each rack in turn past the operation location 34. On completion of the endwise displacement of *the* two *end* racks, each bank of racks 11A, 11B is displaced as a whole at right angles to the stepwise movement by an amount equal to the thickness of a rack so that the original staggered disposition of the banks is regained and the next racks in the sequence are aligned for endwise movement.

At the end of a sequence of operations, the racks can be advanced by the levers and pushrods *13* to the original starting position, the first reaction tube of the first rack in any cassette being identified by a suitable marker; in the preferred form, a magnet location in the rack beneath the first tube provides a signal to a fixed sensor located in the base module. Outward displacement of the banks of racks is prevented by side walls 17 and the two banks are separated by a shallow central partition 18 *terminating short of the end walls 17a to leave the gaps for the endwise displacement of the two end racks into the spaces 11C, 11D as above explained.* Lips 19 on the racks engage under corresponding lips 19A on the side walls and central partition to prevent upward displacement of the racks. The levers and pushrods which move the racks are linked mechanically to switches in the module base which thus sense the position of the racks. In this way, the precise sequence and location of tubes and racks is maintained and made known to the control unit during operational procedures.

In order to transfer the reaction tubes 12 to another base module, it is simply necessary to lift the cassette 14 from one module *at a second or further stations* and engage it in the corresponding location of another. Various sizes of reaction tube can be accommodated within a rack. Disposable moulded plastics racks with integral containers may be used or racks may consist of a "permanent" shoe and a "disposable" multitube component. In one typical cassette arrangement, a total of 420 reaction tubes of 3 ml volume are accommodated with 15 tubes in each of 28 racks.

When it is necessary to seal the tubes, the cassette 14 is placed in a closed box or a lid 21 is fitted to occlude the open ends of all the tubes 12. The lid may consist of a flexible sheet which is pulled taut over the tubes but in the preferred form, a layer of foam rubber 22 is sandwiched between a rigid top sheet 23 and a smooth plastic under lining 24. In this way, effective occlusion of all the tubes can be obtained at a single action and the manual sealing and unsealing of many tubes by individual stoppers is obviated.

The sample processing unit (FIG. 2), consists of (1) sample insertion module 25, (2) dilution module 26, (3) reagent addition module 27, (4) transfer module 28 and (5) filtration module 29.

The insertion module 25 has the following features. A location in the base module 15 for the reaction tube cassette 14, which location provides the means to move the levers and pushrods and switches which advance the tubes in the cassette to and from the operational location. It incorporates a probe unit 30, pump 31 and wash facilities 32 for the transfer of liquid samples 33 to the reaction tube 12 at the operational location 34 without carry-over of solution from one sample to another. The probe 30 carried on a suitable arm and connected by flexible plastic tubing to the pump unit 31 descends into a sample tube 33 at the sample location. The pump withdraws a quantity of the sample in excess of that required for the reaction. The probe is then elevated and rotated through an arc to a wash and wipe location 32 where the probe descends. In this position, two claws faced by a tape 35 of absorbent paper close on the probe. Drops of liquid left on the outside of the probe are thus removed by the absorbent paper when the probe is raised. After elevation of the probe, the claws open and the paper is advanced. The probe then swings through a further arc to the operational location 34 where it descends into the reaction tube 12, the pump discharges the required volume and the probe is lifted and taken back to the wash location where the probe is washed internally and externally by the action if another pump supplying wash fluid and again the probe is wiped on the outside before returning to the sample input location.

The volume of sample dispensed into each reaction tube 12 is determined by the analytical protocol. The same volume may be dispensed into all tubes or varied according to the requirements for dilution. In the preferred form, the pump takes up or discharges a unit volume at each stroke and the control unit controls the number of strokes in each take up and dispensing operation according to assay protocol.

Operation of the sample insertion module 25 is effected by the operator ensuring the Class I and Class II data have been input to the control unit and Class III data pertaining to each sample are typed on the input teleprinter with the sample tube 23 in the sample location. Typing in the command signal, initiates the insertion module sequence.

When a complete batch of reference standards and samples have been dispensed, the racks 11 are returned to their initial sequence and the cassette 14 is transferred manually to the dilution module 26, as indicated by the arrows 20.

The dilution module 26 similarly provides a location for the cassette and means for advancing reaction tubes past the operational location. In order to perform dilutions, one or more pumps add precise amounts of diluent to the sample and other pump or pumps remove similar amounts through a multi-channel probe. Thus a series of dilution steps may be performed. Between each step, the sample and diluent are mixed by the operation of an additional pump with a reciprocating action operating a plunger in one channel of the probe. The volume dispensed or taken up by each pump action may be adjustable over a wide range but, in the preferred form, one or more fixed volumes are dispensed or taken up at each stroke and repetitive strokes are used to give any multiple of these fixed volumes. The operation of the dispensing and takeup pumps is controlled by the control unit 1 according to Class II and III data. Once the dilution sequence has been initiated, no further intervention is required by the operator.

On completion of dilution and return of the reaction tubes 12 to the start position, the cassette 14 is transferred to a corresponding location on the reagent dispensing module 27. As the reaction tubes step to the operational location, one or more reagents are dispensed in the precisely required volume by probe and pump unit of this module. Pump operations may be controlled by settings on the module itself or by programming the control unit. On completion of dispensing and mixing, the occlusive lid 21 is applied to the batch of tubes and the cassette incubated at the desired temperature for the period required. The reagent dispensing module 27 also incorporates a peristaltic pump so that when required a suspension of charcoal or precipitating agent can be dispensed from an agitated solution into the reaction tubes.

On completion of incubation, the cassette 14 is placed on the transfer module 28 from whence the contents of the reaction tubes 12 are transferred to filter locations [36] on the filtration module 29, the action of the two modules being closely integrated. This transfer is effected in the preferred form from five reaction tubes at a time but any convenient number may be used. Five probes descend into five adjacent tubes. The probes are connected by flexible tubes to five corresponding hemispherical domes *37* rigidly mounted on the [filtration unit 37] *module 29*. Each probe contains a second channel through which wash solution is pumped from a supply bottle.

[Filtration is performed at the locations 36 through a cellulose acetate, or glass fibre membranes, or filters of similar porosity, mounted at intervals over perforated segments of a flexible plastic carrier tape 7, and sealed to the tape around the margins of the filters.] *Filtration is performed through a filter material which may be cellulose acetate, a glass fibre membrane or filter of similar porosity mounted at intervals 36 on the tape 7 of strong flexible material, such as polyvinyl chloride, which bears at said intervals a series of locations 43 where the tape is perforated and where the perforations are surmounted by the filter material 44 adherent to the tape at the margins of the filter material.* The carrier tape is further marked at fixed intervals by holes 41 (FIG. 3) or indentations so that its [position] *registration at operational locations* may be precisely controlled by sensors fixed to the filtration module signalling to the control unit. The plastic tape 7 is supplied from a spool 38 and fed through a series of locations to a take up spool, the tape advancing stepwise by five locations at a time. At the first five locations 39 on the filtration module 29, the membranes are wetted with a protein solution. At the second five locations, the five hemispherical domes are sealed against the upper margin of each filter [disc 36] *location* by the elevation of a pressure plate 40 which bears on the lower surface of the filter tape 7. This plate also has five suction areas the peripheries of which seal on the under surfaces of the margins of the filter locations 36 and a cavity within the pressure plate communicates with a vacuum source. Elevation of the pressure plate and activation of the vacuum source causes a negative pressure to be transmitted across the filter [membrane] and for the contents of the reaction tubes 12 to be drawn through the flexible tubing to the filters where the precipitates are retained on the filters. Wash solution is pumped into the reaction tubes and this is also drawn through the filters. Wash solution is also pumped to a series of outlets peripherally disposed at each filter location so as to provide uniform washing over the whole area of the filter [membrane]. In the preferred form, the filtrate proceeds to waste but counting of filtrate radioactivity is an alternative to counting precipitate radioactivity. On completion of filtration and washing, the pressure plate 40 is lowered and the probe assembly on the transfer module 28 elevated. Both tape 7 and reaction tubes 12 then advance five locations. At the next station 42 the filter tape 7 is dried by a fan heater and on emerging from this station, transparent adhesive tape is applied to the filter bearing surface of the carrier tape. After completion of one or more batches of samples, the tape is rewound to its initial sequence and is then transferred to the supply spool position 8 in the radioactivity detector station.

Thus, in the manner just described, radioactive components from a multiplicity of reactions occurring in said tubes are simultaneously transferred to a corresponding multiplicity of filters on the continuous tape. FIG. 1 shows a radioactivity detector station at which photo multiplier devices 5 convert the radioactivity at the multiplicity of filter sites into signals which are accumulated and counted directly in electronic data registers 1. The accumulated totals associated with prior instructions are stored at other locations in the register assembly 1, and computer means 2 performs calculations and transfers the accumulated totals and results of the calculations to appropriate output terminal means denoted at 54.

At the radioactivity detector station, the tape 7 is transported by pinch rollers 53 with drive mechanisms and is thus fed through five counting locations 9. Movement of the carrier type is controlled as on the filtration unit and the counting time is determined by the assay protocol. At each of the five counting locations, there is an opposed pair of photomultiplier tubes 5, the output from which passes via a discriminator 6 and distribution unit to the electronic data register 3 for counting.

Since the counting efficiency of photomultiplier tubes is variable, a tape bearing radioactive filter locations is first advanced one step at a time through the five count locations 9. The relative efficiency of each pair of tubes 5 is thus determined and a correction factor is then applied automatically to the counts received from each location.

When the carrier tape 7 for an assay batch is placed in the detector station of the control unit, the corresponding paper tape is fed into the tape reader on an output teleprinter 54. As radioactivity counting proceeds, the totals for each counting location are associated with the corresponding data on the punch tape. The reference standard line is then computed according to the programme and the concentrations of ligand in the samples are determined and statistical analyses are performed according to standard analytical procedure. The assay data are output to the teleprinter or alternative terminal.

We claim:

1. Apparatus for analysing a plurality of liquid samples, each sample being in a tube, and comprising a cassette having a shell in which a plurality of such tubes are to be contained in sequence, said cassette having apertures in its walls through which means, operated by apparatus external to the cassette, actuate and advance the tubes sequentially and stepwise past a fixed point, said cassette being freely removable from the operating apparatus, without disturbing the contained tubes, to other locations, the initial sequence of tubes being maintained throughout.

2. Apparatus according to claim 1, wherein the cassette is provided with a lid which occludes the open ends of all the tubes contained in the cassette.

3. Apparatus according to claim 1, wherein the cassette carries racks of moulded plastics in which the tubes are an integral part of the rack.

4. Apparatus according to claim 1 wherein said tubes are arrayed in linear series in substantially rigid racks to be received within the cassette shell, and said actuating means advances the racks with the tubes therein sequentially past said fixed point.

5. In combination with the apparatus of claim 1, liquid analysis apparatus comprising at least one module with means to carry out a physical operation on the liquid samples and with a location to receive a selected one of said cassettes at a time and means to actuate operative elements which advance the tubes inside said cassette sequentially past a fixed point.

6. Liquid analysis apparatus according to claim 5 wherein operations of dispensing, transferring and diluting liquid samples are performed by means of pumps actuated by signals received from a control unit which incorporates an electronic data register, according to a sequence of instructions supplied to the control unit by a human operator in at least one prior operation and which instructions may be varied according to the requirements of analytical protocol.

7. Apparatus according to claim 5, wherein liquid transfer and dispensing operations are performed by pumps with fixed stroke volume, multiples of this fixed volume being transferred by repetitive action of such pumps depending on signals from a control unit with a data register operating on prior instructions.

8. Liquid analysis apparatus according to claim 5, comprising means to transfer radioactive components from a multiplicity of reactions occurring in said tubes simultaneously to a corresponding multiplicity of filters on a continuous tape, photomultiplier devices to convert the radioactivity at a multiplicity of filter sites into signals which are accumulated and counted directly in electronic data registers, the accumulated totals associated with prior instructions being stored at other locations in the register, and means to perform calculations and to transfer the accumulated totals and results of the calculations to appropriate output terminals.

9. In combination with apparatus according to claim 8, a tape of strong flexible plastics material, bearing at appropriate intervals a series of locations where the tape is perforated and where the perforations are surmounted by filter discs adherent to the tape at the margins of the filter discs, said tape additionally having holes or indentations to aid in the [correction] *correct* registration of the tape at operational locations.

*10. Analysis apparatus for performing at least two operations on a liquid sample in a sample container comprising first and second support means at respective first and second stations, each support means being adapted to removably receive a cassette having therein a plurality of sample containers, means at substantially fixed points on said respective support means for performing respective first and second operations on the liquid samples in the respective containers, drive means carried by the respective support means and arranged to project into a cassette when on said support means and engage the containers therein for moving the same in a closed path sequentially from an initial relationship to one another past an operation performing means at the fixed points on the respective support means and back to the initial relationship, and means for operating the respective operation performing means upon arrival of a container at each of the respective fixed points.*

*11. Apparatus as claimed in claim 10, wherein the first operation performing means is adapted to dispense samples to be analysed into the containers and the second operation performing means is arranged to dispense a reaction medium into each container.*

*12. Apparatus as claimed in claim 10, wherein the operation performing means each include at least one pump, and control means are provided for controlling operation of the said at least one pump independently for each station.*

*13. Apparatus as claimed in claim 12, wherein the pumps have fixed stroke volumes and multiples of the fixed stroke volume of each pump are dispensed by repetitive action of the pump in dependence on control signals from the control means.*

*14. Apparatus as claimed in claim 10 including a third station at which a third operation is performed on said liquid samples in said sample containers, the apparatus at said third station including support means and drive means substantially identical to said support means and said drive means at said first and second stations.*

*15. Apparatus as claimed in claim 14, wherein the first operation performing means is adapted to dispense samples to be analysed into the containers, the second operation performing means is adapted to dispense a reaction medium into the containers and the third operation performing means is adapted to remove liquid from each container.*

*16. Apparatus as claimed in claim 15, wherein the third station includes means for filtering the liquid removed from each container.*

*17. The apparatus of claim 16 wherein the filtering means comprises a flexible tape bearing at intervals a series of locations where at each interval (1) the tape is perforated*

*and where at each interval (2) a filter defined by porous membrane filter material surmounts the perforations and is adherent to the tape at the margins of the filter.*

*18. A filtration tape for use in radioimmunoassay studies or the like comprising:*

*(a) an elongate carrier tape;*

*(b) the tape having a plurality of longitudinally spaced filtration locations;*

*(c) each such location including:*

*(i) a set of perforations each of which perforations extends through the tape, and*

*(ii) a filter disc overlying each set of perforations and secured to the tape at the margin of the filter disc.*

*19. A tape as claimed in claim 18, including registration means on the carrier tape.*

*20. A tape as claimed in claim 18, wherein the carrier tape has holes or indentations to aid in correct registration of the tape.*

*21. A tape as claimed in claim 18, wherein each filter disc is made of glass fibre.*

*22. A tape as claimed in claim 18, wherein each filter disc is made of cellulose acetate.*

*23. A tape as claimed in claim 18, wherein the carrier tape is made of polyvinyl chloride.*

*24. Portable apparatus for receiving a plurality of linear arrays of sample containers and for permitting circulatory movement of the arrays within the apparatus, the apparatus comprising a rectangular cassette having a base wall and two pairs of opposed side walls defining a space for receiving the arrays, the space within the cassette being divided into two compartments by dividing wall means extending parallel to one pair of opposed side walls and terminating short of each wall of the other pair of side walls to leave a gap, each compartment being adapted to receive a plurality of arrays supported on the base wall and arranged side-by-side, each array extending perpendicular to the dividing wall means and being movable in a direction parallel to the dividing wall means through the respective compartment and from one compartment through the respective gap between the dividing wall means and the respective wall of the other pair of side walls, retaining and guide means for preventing withdrawal of arrays when in the compartments from the compartments and for guiding arrays in their movement through each compartment, and aperture means provided in at least some of the walls for providing access to arrays when in the cassette for means for moving the arrays through the compartments and from one compartment to the other compartment.*

*25. Apparatus as claimed in claim 24, including a lid for closing the open end of containers when in the cassette.*

*26. Apparatus as claimed in claim 24, wherein the retaining and guide means are provided along the one pair of opposed side walls and correspondingly on the dividing wall means.*

*27. Apparatus as claimed in claim 24, wherein the retaining and guide means include a lip extending inwardly of the respective compartment on each of the walls of the one pair of side walls and on the dividing wall means.*

*28. Apparatus as claimed in claim 24, wherein the aperture means are provided in the one pair of opposed side walls.*

*29. In combination with the apparatus as claimed in claim 24, other apparatus for performing at least one operation of dispensing, transferring and diluting a liquid sample, the other apparatus comprising means for performing the operation, means defining a location for receiving the cassette, and means for moving the arrays when in the cassette along a predetermined path past the operation performing means.*

*30. Apparatus as claimed in claim 24, including a plurality of arrays received in the compartments of the cassette, each array being provided with a recess at each end for engagement with the retaining and guide means.*

*31. Apparatus as claimed in claim 30, wherein the arrays are formed of plastics material.*

*32. Apparatus as claimed in claim 30, wherein the arrays define a linear array of receptacles each for receiving a sample container.*

*33. Apparatus as claimed in claim 30, wherein the arrays provide a linear array of sample containers formed integrally therewith.*

*34. A cassette for use in apparatus for analysing a plurality of liquid samples, each sample being in a container, said cassette comprising wall means defining a space for receiving a plurality of such containers, said wall means having aperture means therethrough having through which means, operated by apparatus external to the cassette, will in use actuate and advance the containers sequentially and stepwise past a fixed point, said cassette being adapted to be freely removable from the operating apparatus, without disturbing the containers when contained therein, to other locations, the initial sequence of such containers being maintained throughout.*

*35. A cassette according to claim 34, including a lid for occluding the open ends of containers when contained in the cassette.*

*36. Apparatus comprising a cassette according to claim 34 and arrays of moulded plastic racks to be received within the cassette, the containers being an integral part of the racks.*

*37. Apparatus comprising a cassette according to claim 34 and containers for containing liquid samples, said containers being arranged in linear series in substantially rigid racks to be received in the cassette.*

*38. In combination a cassette according to claim 34 and liquid analysis apparatus comprising at least one module including: means for carrying out a physical operation on a liquid sample, a location to receive said cassette, and means for advancing containers when in said cassette sequentially past a fixed point.*

*39. A method of dispensing a plurality of samples to be analysed and of mixing each sample with a reaction medium, the method comprising, at a first station dispensing a plurality of samples to be analysed into a plurality of containers as they are moved sequentially past a sample dispensing head in a closed path, moving the liquid samples in the containers as a group to a second station, at the second station moving the samples in the containers in the order in which they were dispensed past a reaction medium dispensing head in a closed path, dispensing the reaction medium into the containers, and removing the liquid samples and reaction medium in the containers as a group from the second station.*

*40. A method as claimed in claim 39, including removing the samples and reaction medium from the containers, wherein the samples and reaction medium in the containers are moved as a group from the second station to a third station and, at the third station the containers containing the samples and reaction medium are moved past a removing head in the order in which they were dispensed and in a closed path.*

*41. A method as claimed in claim 40, wherein the containers are moved between the stations manually.*

*42. A method as claimed in claim 40, wherein, between the second and the third stations, the containers are placed as a group in an incubator.*

*43. A method of mixing a plurality of samples to be analysed with a reaction medium and withdrawing the mixture, the method comprising placing containers containing the samples in a first station, at the first station moving the samples in the containers sequentially past a reaction medium dispensing head, dispensing reaction medium into the containers, moving the containers as a group from the first station and placing them in a second station, at the second station moving the sample containers sequentially past a sample withdrawing head in the same order as that in which the sample containers moved through the first station, and withdrawing the samples and reaction medium from the containers.*

*44. A method as claimed in claim 43, wherein the sample mixtures withdrawn from the containers in the second station are filtered and the components retained by the filter means are analysed.*

*45. A method as claimed in claim 44, wherein the reaction medium is radioactive and the radioactivity of the filter means is determined.*

*46. Analysis apparatus for performing at least one operation on a liquid sample in a sample container said apparatus comprising support means for removably receiving a cassette having therein a plurality of sample containers, means for performing the operation disposed at a substantially fixed point on said support means, drive means carried by said support means and arranged to project into a cassette on said support means and engage the containers therein for moving the same in a closed path sequentially from an initial relationship to one another past the operation performing means at said fixed point and back to the initial relationship, and means for operating said operation performing means upon arrival of a container at said fixed point.*

*47. Apparatus as claimed in claim 46 wherein the support means comprises a base module, said base module being one of a plurality of substantially similar base modules, each being adapted to removably receive a cassette transferred thereto from another of said base modules.*

*48. A method of performing at least two operations on a liquid sample in each of a plurality of liquid sample containers, the method comprising arranging the sample containers in a predetermined sequence in a portable cassette, removably positioning the cassette at a first station adjacent means for performing a first operation, moving the liquid sample containers in a closed path in the cassette sequentially past the first operation performing means, performing the first operation on the containers, moving the cassette with the liquid sample containers as a group therein from the first station and positioning them in a second station adjacent means for performing a second operation, moving the liquid sample containers in a closed path in the cassette sequentially past the second operation performing means, performing the second operation on the containers, and moving the cassette with the liquid sample containers as a group therein from the second station.*

*49. Filtration means for use in radioimmunoassay studies or the like comprising:*

*(a) a strong flexible tape bearing at intervals a series of locations where at each interval:*

(i) the tape is perforated; and where at each interval (ii) a filter disc defined by porous membrane filter material surmounts the perforations and is adherent to the tape at the margins of the filter disc.

*50. Filtration means as claimed in claim 49, including registration means on the carrier tape.*

*51. Filtration means as claimed in claim 49, wherein the carrier tape has holes or indentations to aid in correct registration of the tape.*

*52. Filtration means as claimed in claim 49, wherein each filter disc is made of glass fibre.*

*53. Filtration means as claimed in claim 49, wherein each filter disc is made of cellulose acetate.*

*54. Filtration means as claimed in claim 49, wherein the carrier tape is made of polyvinyl chloride.*

* * * * *

UNITED STATES PATENT AND TRADEMARK OFFICE

CERTIFICATE OF CORRECTION

PATENT NO. : RE 30,627

DATED : May 26, 1981

INVENTOR(S) : Kenneth D. Bagshawe and James E. Kemble

It is certified that error appears in the above-identified patent and that said Letters Patent are hereby corrected as shown below:

Please amend claim 49 so that paragraphs (a)(i) and (a)(ii) are in italics

Signed and Sealed this

*Twenty-ninth* Day of *September 1981*

[SEAL]

*Attest:*

GERALD J. MOSSINGHOFF

*Attesting Officer*

*Commissioner of Patents and Trademarks*